United States Patent [19]

Bonnell

[11] Patent Number: 4,506,673

[45] Date of Patent: Mar. 26, 1985

[54] THERAPEUTIC TREATMENT WITHIN JOINT CAPSULES OF THE BODY

[75] Inventor: Leonard J. Bonnell, Huntingdon Valley, Pa.

[73] Assignee: Rorer Group Inc., Fort Washington, Pa.

[21] Appl. No.: 434,951

[22] Filed: Oct. 18, 1982

[51] Int. Cl.³ .......................... A61N 1/20; A61N 1/04
[52] U.S. Cl. .................................. 128/419 F; 128/784
[58] Field of Search ............... 128/419 F, 787, 419 R, 128/82.1, 784

[56] References Cited

U.S. PATENT DOCUMENTS

| | | | |
|---|---|---|---|
| 3,654,933 | 4/1972 | Hagfors | 128/419 C |
| 3,774,618 | 11/1973 | Avery | 128/419 C |
| 3,842,841 | 10/1974 | Brighton et al. | 128/419 R |
| 3,881,495 | 5/1975 | Pannozzo et al. | 128/422 |
| 3,890,953 | 6/1975 | Kraus et al. | 128/419 F |
| 3,893,462 | 7/1975 | Manning | 128/421 |
| 4,026,304 | 5/1977 | Levy | 128/419 F |
| 4,105,017 | 5/1977 | Ryaby et al. | 128/419 F |
| 4,153,060 | 8/1978 | Korostoff et al. | 128/419 F |
| 4,244,373 | 5/1979 | Nachman | 128/419 F |
| 4,306,564 | 12/1981 | Kraus | 128/419 F |
| 4,308,868 | 1/1982 | Jhabvala | 128/421 |

FOREIGN PATENT DOCUMENTS

| | | | |
|---|---|---|---|
| 480202 | 3/1975 | Australia | 128/419 F |
| 2347214 | 3/1974 | Fed. Rep. of Germany . | |
| 2552523 | 8/1976 | Fed. Rep. of Germany | 128/419 F |
| 138275 | 3/1978 | German Democratic Rep. . | |
| 618610 | 1/1978 | Switzerland . | |
| 2053687 | 2/1981 | United Kingdom . | |
| 2054378 | 2/1981 | United Kingdom . | |
| 161472 | 6/1961 | U.S.S.R. . | |
| 554870 | 9/1975 | U.S.S.R. . | |
| 565665 | 9/1975 | U.S.S.R. . | |
| 643156 | 9/1977 | U.S.S.R. . | |
| 665917 | 11/1977 | U.S.S.R. . | |
| 668690 | 2/1978 | U.S.S.R. . | |
| 731975 | 11/1978 | U.S.S.R. . | |
| 736984 | 11/1978 | U.S.S.R. . | |

OTHER PUBLICATIONS

Final Report, "The Use of Electrical Bone Growth Stimulators in Non Union Fractures", SSIE No. 44500, May 1981.
"A Conversation with Carl T. Brighton, M.D.: Direct Current Bone Growth Stimulation in the Treatment of Fracture Non-Union", Orthopaedic Review, vol. X, No. 2, Feb. 1981, pp. 97–103.
Osteostim, by Osteostim, Division of Telectronics Proprietary Ltd., Ad in Journal of Bone and Joint, #1, 1981.
B₁-Osteogen System, by Electro-Biology, Inc., Ad in Journal of Bone and Joint, #1, 1981.
Zimmer Direct Current Bone Growth Stimulator, by Zimmer, Inc., Ad in Journal of Bone and Joint, #3, 1981.
Closeout Report, "Research on Improved Electromagnetic Instrumentation to Accelerate Bone Repair," NSF Award No. NSF-APR-76-19469, Dec. 23, 1980.
Herskowitz, L., "It's Electric: Bone Coaxed Into Healing", Philadelphia Inquirer, Dec. 8, 1980.
Weymouth, L., "The Electrical Connection", New York, Dec. 1, 1980, pp. 44–58, and Nov. 24, 1980, pp. 26–47.
Othofuse, by DuPuy, Division of Boehinger Mannheim Corporation, Ad in Orthopaedic Review, Nov. 1980.
Initial Report, "Direct Current Bone Stimulation in Treatment Ununited Fracture", SSIE No. 46955, Oct. 1980.
Treharne, Richard, "Application of Electric Currents to in vitro Fetal Rat Tibiae", Univ. of Penn., PhD Dissertation, 1976.

Primary Examiner—Lee S. Cohen

[57] ABSTRACT

A method for stimulating formation of tissue in a living being within a joint capsule includes the steps of: introducing at least a cathode terminal into the joint capsule from the exterior through a puncture in the flesh, under visual control of an arthroscope introduced into the joint capsule via a puncture in the flesh, juxtaposing the cathode terminal in close relationship to a region in the capsule where tissue growth is desired, positioning an anode terminal at a location remote from but in substantial electrical continuity, through body tissue, with the cathode terminal, and connecting an electric power supply between the anode and cathode terminals, the steps being adapted to cause electrical current to flow between the terminals in a manner to stimulate growth of tissue on the surface. A device for introduction into the joint capsule for stimulating formation of tissue according to the invention is also disclosed.

25 Claims, 8 Drawing Figures

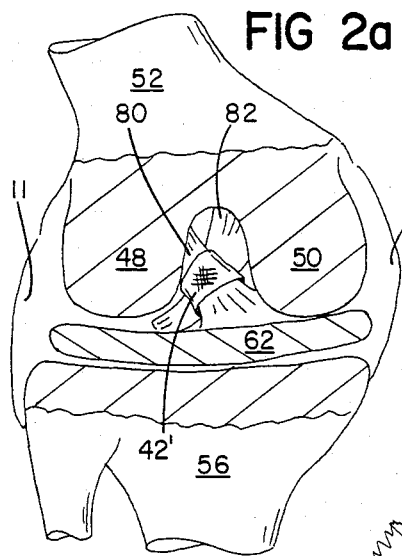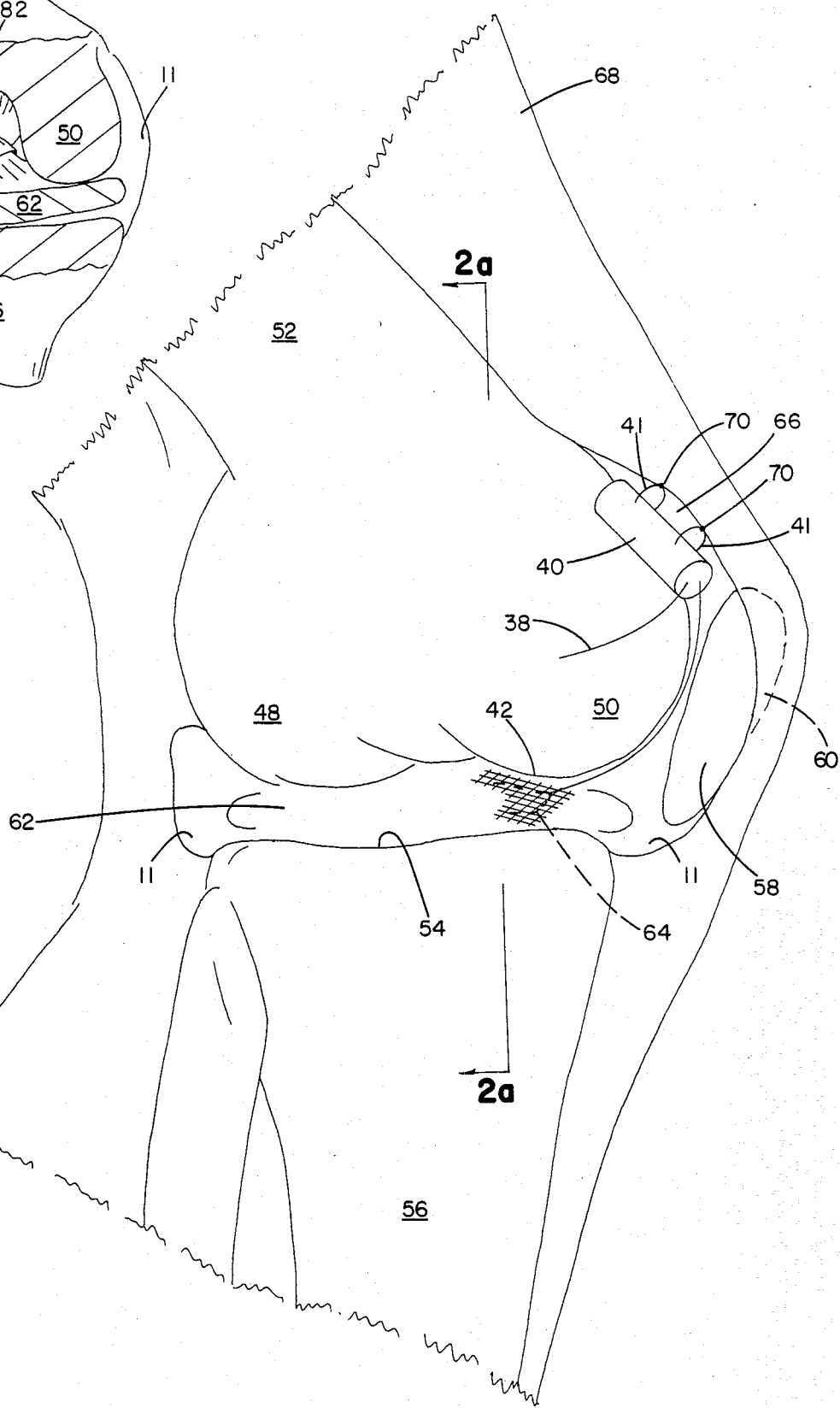

THERAPEUTIC TREATMENT WITHIN JOINT CAPSULES OF THE BODY

The invention relates to therapeutic treatment within joint capsules of living bodies.

According to the invention, for stimulating formation of tissue a cathode terminal is introduced into the joint capsule from the exterior through a puncture in the flesh, under visual control of an arthroscope introduced via a puncture in the flesh, the cathode is juxtaposed in close relationship to a surface or portion of the body within the joint capsule where tissue growth is desired, an anode terminal is positioned at a location remote from but in substantial electrical continuity, through body tissue, with the cathode terminal, and an electric power supply is connected between the anode and cathode terminals to cause electrical current to flow between the terminals to stimulate the growth of tissue in the desired region within the joint capsule.

Preferably the anode is also introduced into the joint capsule through a puncture in the flesh and is positioned arthroscopically, ordinarily in a position remote from relatively movable surfaces of the joint.

In preferred embodiments of the invention, the cathode terminal comprises an array of conductive regions juxtaposed in face-to-face overlying relationship to a surface where formation of tissue is desired, which may be a relatively movable surface of a joint. In some cases, the cathode terminal is introduced in a preformed, compacted state into the joint capsule through a puncture, and is then deployed or spread into overlying relationship with the region where growth is desired. In other cases, the cathode is formed as an array of separate conductive elements that are assembled within the joint capsule by arthroscopically guided installation of the individual elements. In either case the cathode may be cut or otherwise shaped to approximate the shape of the defect upon which tissue formation is desired. Where the terminal is a preformed array, the cathode terminal is preferably of flexible sheet form. In some instances the cathode may be adapted also to provide a closed, protective covering to isolate the region where growth is to occur, e.g. in the case of a ligament, the protective covering is wrapped around the ligament to isolate the region from the remainder of the joint capsule. In other cases the preformed array may be an open, conductive grid having at least 75% open area. In the various cases, the method preferably includes the further step of fastening the cathode terminal to the surface upon which tissue growth is desired, preferably by a biodegradable fastener. The cathode is also preferably of a biodegradable substance.

In preferred embodiments where the method is directed to growth of cartilaginous tissue within the joint capsule, the surface upon which cartilaginous tissue is to be formed can be the tibeal plateau, a condyle surface of the femur or the undersurface of the patella. In particular, the surface may be a load-bearing articular surface. Preferably, on some surfaces, prior to inserting and applying the device, the surface is subjected to abrasion arthroplasty by which underlying vascularity is exposed by the action of a moving abrading element. Where the method is applied to a torn meniscal cartilage, the torn portion of the meniscus having first been secured to the original base from which it has been torn, the cathode terminal is thereafter juxtaposed in close relationship to the region of tear to stimulate growth of tissue between the torn portion and the base. Where a portion of cartilage such as the meniscal cartilage is excised, the cathode is thereafter juxtaposed over the region formerly occupied by the excised portion of cartilage, for stimulating growth of cartilaginous tissue in the region.

After stimulation of tissue growth, the grown tissue may be shaped by use of arthroscopically guided instruments, e.g. suctioning and cutting or scraping instruments.

In preferred embodiments, the electrical power supply means comprises at least a battery and the method comprises the further steps of introducing the power supply means into the joint capsule from the exterior via a puncture in the flesh, and securing the power supply means under visual control of the arthroscope within the joint capsule. Preferably, for growth of tissue within the knee joint, the power supply means is positioned within the joint capsule of the knee in the suprapatellar pouch, alongside the quadriceps muscle. Preferably, the electric current is established at 20 microamps or less; the current is applied to the surface for an extended period of duration of less than about 10 weeks; and the joint is partially immobilized by use of a brace, without use of a cast.

Electrical energy has been used in other, distinctly different fields for therapeutic treatment of disorders, e.g. Jhabvala U.S. Pat. No. 4,308,868 and Avery U.S. Pat. No. 3,774,618 show implantable electrodes for growth stimulation in regions of damaged or severed nerves in animals. Implantable and noninvasive devices have been used in the case of non-unions of bone fractures, i.e. fractures that will not heal, to stimulate growth of bone tissue. The invasive devices are typically implanted by standard open surgery procedures during which the defect is laid open surgically, the device implanted, and the wound surgically closed. The procedure must be repeated to maintain or remove the device. A period of patient immobility is required after each surgical procedure to allow the wounds to heal. Noninvasive devices typically use fixed treatment apparatus which limits mobility of the patient, e.g. the system supplied by Electro-Biology International, Ltd., and others, e.g. as shown in Ryaby et al. U.S. Pat. No. 4,105,017. These, too, often require open surgery for positioning of field concentrating devices.

Features and advantages of the present invention will be apparent from the description of the preferred embodiment that follows, and from the claims.

DESCRIPTION OF THE PREFERRED EMBODIMENTS

We first briefly describe the drawings.

FIG. 2 is an enlarged representation of a knee capsule showing an implanted device on the meniscal cartilage, while FIG. 2a is a sectional view taken at line 2a-2a of FIG. 2 showing a cathode terminal wrapping a ligament;

Figure 3:
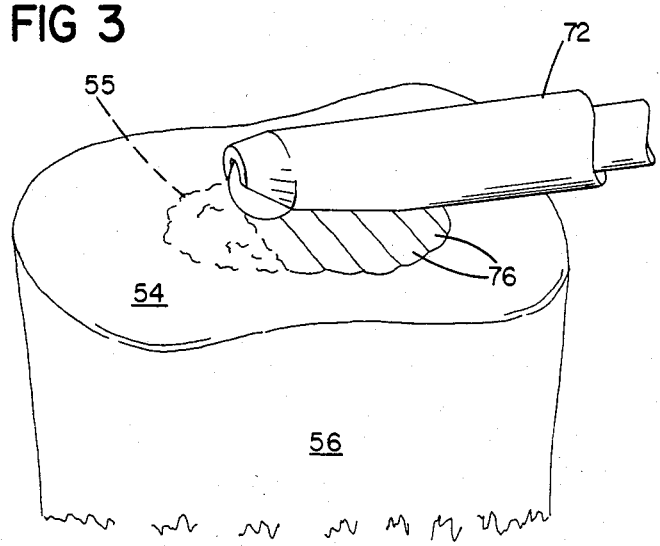
Figure 3A:
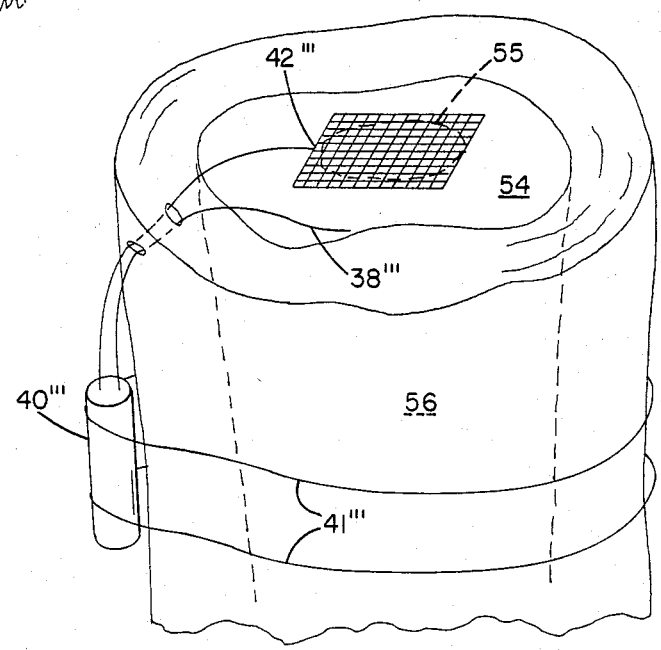
Figure 4:
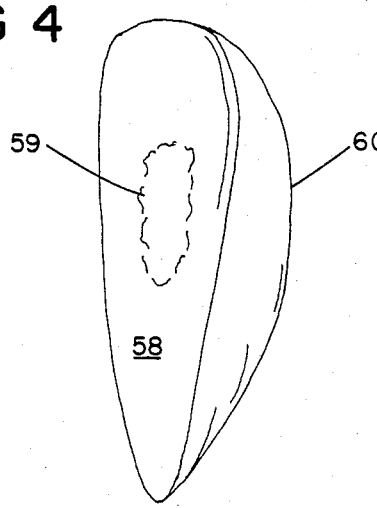
Figure 4A:
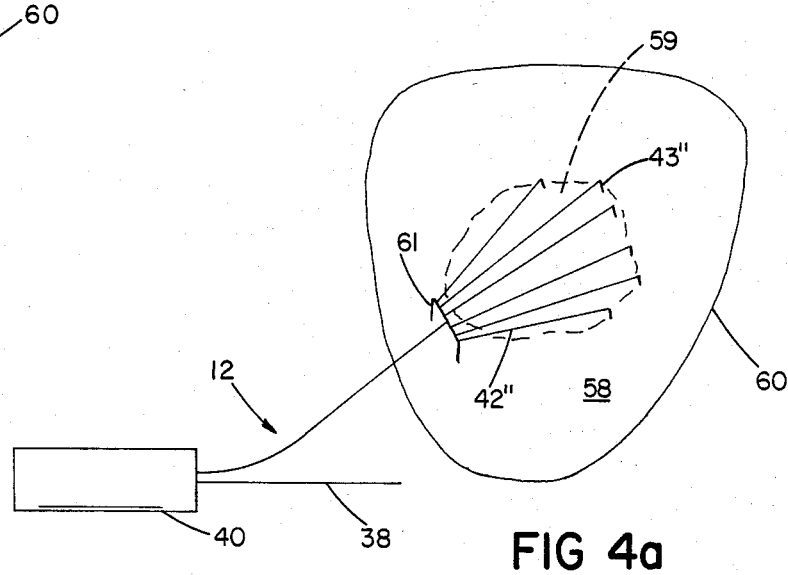

FIG. 3 is a perspective view of a tibeal plateau in the knee capsule during abrasion anthroplasty to expose the profuse vascularity underlying the defect in the tissue on the surface thereof, while FIG. 3a is a diagrammatic perspective view of the tibeal plateau showing still another embodiment of the device; and FIG. 4 is a diagrammatic perspective view of a patella, i.e. kneecap, having a defect on the rear surface thereof, while FIG. 4a is a diagrammatic rear view of the patella of FIG. 4 showing another embodiment of the device.

STRUCTURE

Figure 1A:
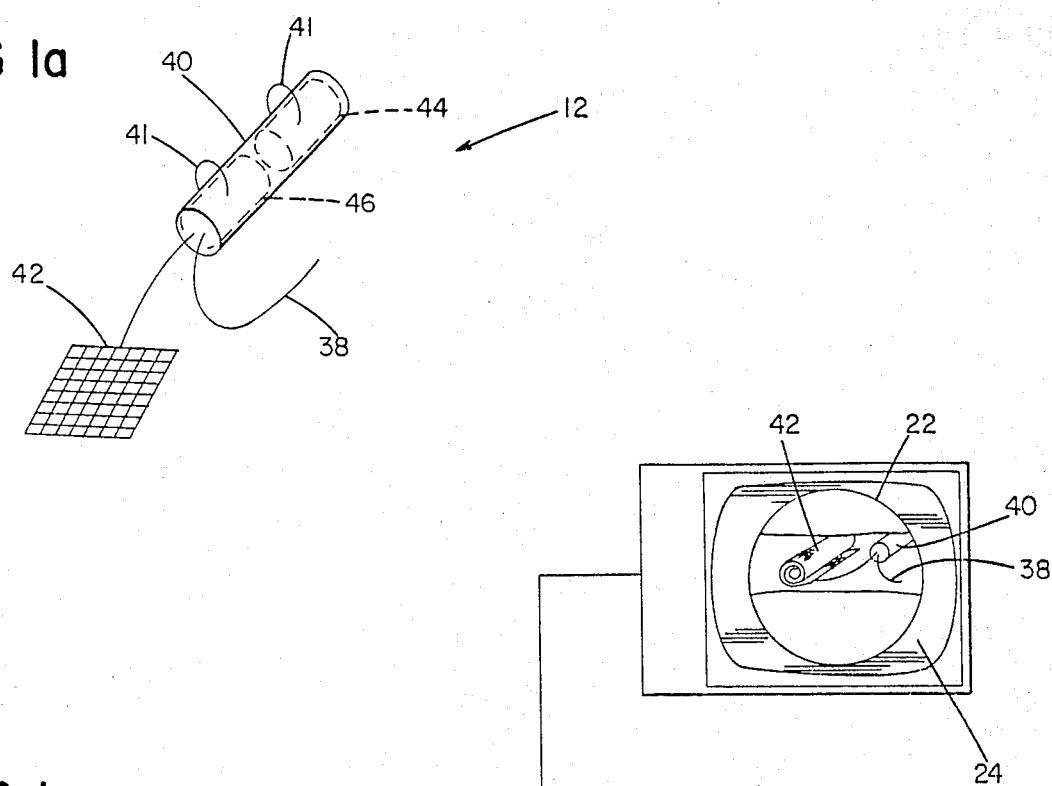
FIG. 1a is a perspective view of a preferred embodiment of the device of the invention.
Figure 1:
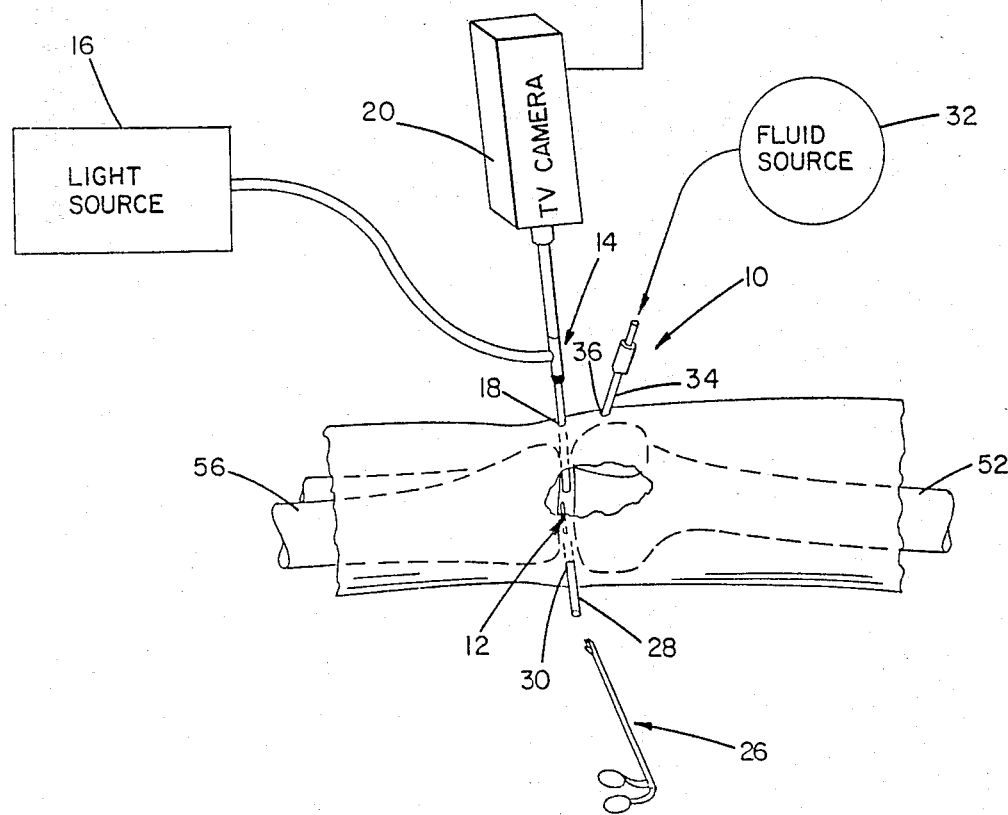
FIG. 1 is a diagrammatic view showing the implantation of a device for stimulation of tissue formation in the knee capsule employing arthroscopic procedures.

Referring to FIG. 1, knee joint 10 is prepared for arthroscopic surgery. An arthroscope 14 introduces light from light source 16 to the interior capsule 11 of joint 10 through a small puncture 18 in the flesh and returns a visual image along a separate optical path. While the image can be directed to an eye piece for the surgeon, as well as to a recording camera, in the preferred embodiment shown, the image is directed to television camera 20 which creates the display 22 on television monitor 24 which the surgeon watches to control his movements. By thus watching the screen, the surgeon can manipulate grasping forceps 26 inserted into capsule 11 through cannula 28 (which is inserted through another small puncture 30 in the flesh) to position stimulation device 12 (see FIG. 1a) within the joint capsule. Inflation fluid, e.g. liquid or a gas, from source 32 is introduced into the joint capsule 11 through a third cannula 34 through puncture 36 to distend the joint for improved access and vision. A flow of liquid through joint 10 may first be used to distend the joint and to flush away blood or other substances. At the option of the surgeon this flow may be terminated and gas introduced to maintain the distension of the joint while the stimulating device is deployed.

Referring now to FIGS. 1 and 1a, stimulation device 12 comprises an anode terminal 38 and a cathode terminal 42 both connected to power source 40. The cathode 42 is a mesh, typically with 75 to 90% open area, made of biodegradable, electrically conductive substance of a suitable kind, for instance cotton fiber impregnated with fine carbon particles to provide electrical conductivity. The material is selected for its compatability with living tissue and because it is biodegradable over time and therefore does not require additional surgical procedures for removal at the end of the treatment period. Anode 38 is a pseudo-wire of the same material. Power source 40 is provided with a biocompatible outer case, typically made of titanium, sized, typically about 5.0 mm diameter and 15 to 24 mm long for use in the knee, for insertion into joint capsule 11. The power source may be inserted directly through cannula 28 as shown, or through puncture 30. The case contains a battery 44 and control device 46 capable of maintaining the output of source 40 at a constant current level, e.g. 20 microamps, over an extended period, while the impedence of the tissue connected between the anode 38 and cathode 42 increases as tissue growth is stimulated. (Examples of larger power source devices commercially available for stimulation of bone growth, e.g. for nonunions, are Osteostim Model S-12 from Osteostim, division of Telectronics Proprietary Ltd., of Englewood, Calif. and Orthofuse from DeDuy, division of Boehringer Mannhein Corp., of Warsaw, In.)

Referring now to FIG. 2, knee joint 10 is shown in an enlarged view. The joint space containing capsule 11 is generally defined by condyles 48, 50 at the lower end of femur (thigh bone) 52, the tibeal plateau 54 at the upper end of tibia (shin bone) 56, and the undersurface 58 of patella (kneecap) 60. Each of these surfaces has a layer of cartilaginous tissue which acts to cushion contact with adjacent surfaces of other members. The capsule also contains the medial and anterior sections of the meniscal cartilage 62, which forms a load-bearing surface between the femur 52 and the tibia 56, and, referring to FIG. 2a, the anterior and posterior cruciate ligaments 80, 82 which connect these bones. Defects in any of these surfaces due, e.g., to physical injury or to disease, generally lead to patient discomfort and can impair physical activity, including walking in severe cases.

Arthroscopic surgical procedures and specialized instruments for performing arthroscopic surgery upon these joint surfaces have been developed by myself and others. For example see U.S. Pat. Nos. 4,203,444 ("Surgical Instrument Suitable for Closed Surgery of the Knee") and 4,274,414 ("Surgical Instrument"), and also U.S. patent application Ser. Nos. 239,895 ("A Surgical Instrument for Arthroscopic Arthroplasty", filed Feb. 25, 1981) and U.S. Pat. No. 334,512 ("Surgical Debridement Instrument for Orthopedic Surgery", filed Dec. 28, 1981).

OPERATION

Referring back to FIG. 1, the punctures in the flesh for insertion of the arthroscope and instruments are started with a sharp trocarring instrument placed inside a cannula, and pushed, as a unit, into the flesh. The trocar is removed leaving the cannula (a thin tubing) forming an opening into the joint. If necessary the opening can be deepened with a blunt obturator. An arthroscope is inserted into the cannula and the surfaces within joint capsule 11 are visually inspected by the surgeon as he manipulates the arthroscope 14 and observes the display 22 on television monitor 24. A defect found in a joint surface may be dealt with surgically by arthroscopic procedures, as discussed more fully below, by use of an instrument inserted through cannula 28 and controlled by the surgeon by observing image 22. After the instrument is withdrawn, the surgeon inserts device 12 into the joint space through cannula 28 using grasping forceps 26. Cathode 42 is typically inserted in compacted form, e.g. in a roll, which must be deployed within the joint capsule under visual control of the surgeon before being positioned over the defect by use of forceps 26 and fixed in position. Anode 38 is preferably also positioned within the joint space, either on bone or on a soft tissue surface, at a point remote from cathode 42 but within substantial electrical continuity therewith through the joint tissue. Power source case 40 is also positioned and fixed within the joint space by means of straps 41 provided for that purpose.

The arthroscope 14 and cannulas 28, 34 are then withdrawn and the punctures 18, 30, 36 are closed. The patient's leg is fixed by means of a brace (not shown) set for a chosen range of angles that allow mobility of the patient but prevent relative movement of the joint surfaces that would disturb placement of device 12.

Power source 40 generates a constant current, e.g. of 20 microamps, to flow between anode 38 and cathode 42 which stimulates formation of tissue about cathode 42. Treatment typically may last for an extended term of up to ten weeks but the brace is necessary only until sufficient tissue is formed over the cathode to hold it in place.

After completion of the extended term of treatment prescribed by the attending physician, the treated area may be reinspected by the surgeon arthroscopically. If treatment is satisfactorily complete, the power source 40 may be removed from the joint through a puncture in the flesh. The anode 38 and cathode 42 are biodegradable and thus need not be removed.

EXAMPLES

By way of example, arthroscopic surgical procedures for alleviating defects affecting different surfaces of the knee joint are described. The invention is, of course, not limited to use in conjunction with these procedures, or to procedures only of the knee.

Meniscal Cartilage

Referring again to FIG. 2, the meniscal cartilage 62 extends between the bones 52, 56 of the knee. Damage to this cartilage typically appears as a tear along the rim of the cartilage, described as a "parrot-beak" or "bucket handle" tear.

If the tear is small, i.e. extending for well less than one third of the way around the rim, the surgeon may elect to suture the tear closed. After the surgeon closes the tear 64, he prepares device 12 by cutting cathode mesh 42 to fit the shape of tear 64. The cathode is folded or rolled to fit through cannula 28 and the entire device 12 is inserted into joint 10. Using forceps 26 and observing the image on screen 24, the surgeon unrolls the cathode and positions it over the sutured tear 64. The cathode is fixed in place using staples, typically stainless steel or collagen, which is biodegradable. Anode 38 is positioned within the joint capsule at a point somewhat remote from cathode 42, but within a distance to allow electrical conductance through the intervening tissue. Power source 40 is positioned in the quadriceps pouch 66, formed by the quadriceps muscle 68 along side the patella 60, and held in place by suture stitches 70 taken through straps 41.

Current generated by source 40 to flow from anode 38 to cathode 42 through the intervening tissue stimulates formation of tissue along the suture line to thus close the tear.

Where the tear extends for a longer distance around the rim, i.e. about one third or more, the loose flap may be excised arthroscopically by the surgeon, e.g. using a Meniscal Cutter surgical instrument manufactured by Dyonics, Inc., of Andover, Mass., or other suitable instrument. When the flap is removed, the surgeon forms the cathode 42 to fit over the excision. The entire device is inserted into the joint space and positioned as before. Electric current generated by source 40 stimulates formation of cartilaginous tissue along the point of incision to reduce the open, uncushioned area between the bone surfaces of the knee. (The portion of meniscal cartilage remaining after the incision procedure may also undergo some flattening to reduce the open area.) After a period of tissue formation it may be necessary for the surgeon to trim the new tissue arthroscopically to form a more uniform cushioning surface, e.g. by use of the Shaver instrument also manufactured by Dyonics, Inc., or other suitable instrument.

After the cathode is positioned and the instruments withdrawn, the patient's knee is fit with a brace to restrict angular mobility. This is necessary during early stages of tissue formation to avoid disturbing cathode 42 which is, of course, on a load-bearing surface. The brace does not adversely affect the patient's ability to walk, and, in fact, patients having arthroscopic surgery are typically able to walk within at most a few days and in some cases within hours. (This compares favorably with conventional surgery which restricts the patient completely for at least several weeks.)

Bone Surfaces

The bone surfaces of the knee joint, i.e. the tibeal plateau 54 and the condyles 48, 50 of the femur 52, are subject to deterioration of their covering cartilage. In U.S. patent application Ser. No. 239,895 (cited above), a novel instrument (72, FIG. 3) and procedure for corrective arthroscopic procedures for these surfaces were described for exposing, over an extended surface area, the profuse underlying vascularity by removing a thin layer of degenerated cartilage and bone to facilitate regeneration of fibro-cartilage or cartilaginous tissue on the joint surface.

As shown in FIG. 3, the surface 54 of tibia 56 has an area 55 of defective cartilage which is being abraded by use of suctioning instrument 72 with a rotating abrasive head 74, e.g. an Abrader instrument, also manufactured by Dyonics, Inc., to a depth of about 0.4 mm over an area of several millimeters in both lateral directions to expose the underlying vascularity 76. As in the above examples, cathode 42 is positioned over the defect, while the anode 38 is positioned in the joint capsule remote from the cathode but within electrical continuity through the intervening tissue.

Patella

Referring to FIG. 4, the undersurface of the patella 60, although not a load-bearing surface, develops growths that affect the patient's comfort. These growths may be removed arthroscopically, e.g. by means of the Dyonics Shaver instrument.

As described above, the device 12 is inserted into the joint 10 and the cathode is positioned over the defect to stimulate formation of cartilaginous tissue.

Ligaments

Referring back to FIG. 2a, the anterior and posterior cruciate ligaments 80, 82 extend into joint capsule 11. These ligaments are subject to damage, e.g. tearing, which limits stability of the knee.

As described above, device 12 is inserted into joint capsule 11. In this case cathode 42' is typically a solid blanket, e.g. of collagen, having an array of conductive regions on its surface. The blanket is inserted into the capsule in roll form. The surgeon unrolls the blanket within the capsule and then, under visual control of the arthroscope, wraps the cathode terminal about the portion of the ligament to isolate and protect it during tissue formation.

OTHER EMBODIMENTS

Other embodiments of the invention are within the following claims. For example, the cathode may take other forms, e.g. in FIG. 4a cathode 42" terminates in a series of individual wires which are arranged over the defect 59 on the undersurface 58 of patella 60. The wires, which typically are made of cotton impregnated with fine carbon but can be any suitable, conductive, biodegradable material, have non-conductive, fluonine-containing-resin-coated hardened tips 43" which are embedded directly into the patella surface. The wires are gathered by staple 61, also driven into surface 58. The cathode may also have the form of a single wire. As shown in FIG. 3a, the power source 40''' may be positioned outside the body of the patient, secured by encircling straps 41''', with the anode 38''' and cathode 42''' connected through the skin. In this embodiment, no additional arthroscopic procedure would be required to remove the source case. Also, the anode may be positioned outside the joint capsule where desired. A source adapted to deliver pulses of direct current or alternating current through the device may also be employed.

What is claimed is:

1. A method for stimulating formation of tissue in a living being within a joint capsule comprising the steps of:

Providing means for conducting electrical current comprising at least an anode terminal and a cathode terminal, introducing at least the cathode terminal into said joint capsule from the exterior through a puncture in the flesh of the living being, under visual control of an arthroscope introduced into said joint capsule via a puncture in the flesh, juxtaposing said cathode terminal in close relationship to the region within said joint capsule where said tissue growth is desired, positioning said anode terminal at a location remote from but in substantial electrical continuity, through body tissue, with said cathode terminal.

connecting an electric power supply means between said anode and cathode terminal, said steps being adapted to cause electrical current to flow between said terminals, through said region of the body to stimulate growth of tissue thereon.

2. The method of claim 1 wherein said anode terminal is also introduced into the joint capsule through a puncture in the flesh and is positioned arthroscopically at a location remote from relatively movable surfaces of said joint.

3. The method of claim 1 wherein said cathode terminal provides an array of conductive regions juxtaposed in face-to-face overlying relationship with a surface where formation of said tissue is desired.

4. The method of claim 3 wherein said cathode terminal comprises means defining a preformed array of conductive regions introduced in a compacted state into said joint capsule through a puncture in the flesh of said living being, said method further comprising deploying said cathode terminal when within said joint capsule from the compacted state into said close relationship.

5. The method of claim 4 wherein said cathode terminal is of flexible, sheet form.

6. The method of claim 5 wherein said cathode terminal provides a protective covering to isolate a part of the body within said joint capsule.

7. The method of claim 6 wherein said part of the body is a ligament and said protective covering is wrapped around the ligament to isolate said ligament.

8. The method of claim 4 wherein said cathode terminal is an open, conductive grid having at least 75% open area.

9. The method of claim 3 wherein an array of conductive regions forming said cathode terminal is comprised of a multiplicity of separate elements, said method comprising assembling said array in situ within said joint capsule.

10. The method of claim 3 wherein said method includes cutting or otherwise shaping said cathode terminal to approximate the shape of a defect upon which tissue growth is desired.

11. The method of claim 1 or 3 comprising the further step of fastening said cathode terminal to a surface upon which said tissue growth is desired.

12. The method of claim 11 wherein said fastening is provided by a biodegradable fastener.

13. The method of claim 1 or 3 wherein said cathode terminal is of a biodegradable substance.

14. The method of claim 1 or 3 directed to growth of cartilaginous tissue within the joint capsule of a living being, the surface upon which said cartilaginous tissue is to be formed being the tibeal plateau, a condyle surface of the femur or the undersurface of the patella.

15. The method of claim 14 wherein said surface of said joint upon which said cartilaginous tissue is to be formed is a load-bearing articular surface.

16. The method of claim 14 wherein, prior to said steps, said surface upon which said cartilaginous tissue is to be formed is subjected to abrasion arthroplasty by which underlying vascularity is exposed by the action of a moving abrading element.

17. The method of claim 14 wherein after stimulation of growth of said tissue, the grown tissue is shaped by use of an arthroscopically guided, shaping instrument.

18. The method of claim 1 applied to a torn meniscal cartilage in which the torn portion of the meniscus is first secured to the original base from which it has been torn and thereafter said cathode terminal is juxtaposed in close relationship to the region of tear to stimulate growth of tissue between said torn portion and said base.

19. The method of claim 1 in which a portion of cartilage such as the meniscal cartilage is excised and thereafter said cathode terminal is juxtaposed over the region formerly occupied by said excised portion of said cartilage, for stimulating growth of cartilaginous tissue in said region.

20. The method of claim 18, or 19 wherein after stimulation of growth of said tissue, the grown tissue is shaped by use of an arthroscopically guided, shaping instrument.

21. The method of claim 1 wherein said electrical power supply means comprises at least a battery and the method comprises the further steps of introducing said power supply means into said joint capsule from the exterior via a puncture in the flesh, and securing said power supply means under visual control of said arthroscope within the joint capsule.

22. The method of claim 21 directed to growth of said tissue within the knee joint wherein said power supply means is positioned within the joint capsule of the knee in the suprapatellar pouch, alongside the quadriceps muscle.

23. The method of claim 21 or 22 comprising establishing the electric current at 20 microamps or less.

24. The method of claim 1 including applying said current to said region for an extended period of duration of less than about 10 weeks.

25. The method of claim 1 in which said joint is partially immobilized by use of a brace, without use of a cast.

* * * * *